United States Patent [19]

Collins et al.

[11] Patent Number: 4,483,853

[45] Date of Patent: Nov. 20, 1984

[54] AMINO ACID ISOMERS, THEIR PRODUCTION AND THEIR MEDICINAL USE

[76] Inventors: James F. Collins, Flat 7, Langwood, 87 Langley Rd., Watford, Hertfordshire, England; Kenneth Curry, University of British Columbia, Department of Physiology, Vancouver, British Columbia, Canada; Robert Schwarcz, 6719 Bonnie Bridge Dr., Apt. 202, Baltimore, Md. 21209

[21] Appl. No.: 434,361

[22] Filed: Oct. 14, 1982

Related U.S. Application Data

[63] Continuation-in-part of Ser. No. 356,036, Mar. 8, 1982.

[30] Foreign Application Priority Data

Aug. 14, 1981 [GB] United Kingdom ............... 8124899
Aug. 11, 1982 [DE] Fed. Rep. of Germany ....... 3229893

[51] Int. Cl.$^3$ .................... A61K 31/66; A61K 31/16; A61K 31/19; A61K 31/22
[52] U.S. Cl. ................................... 424/211; 548/253; 260/502.3; 260/502.5 G; 260/513 N; 260/961; 260/970; 424/185; 424/269; 424/311; 424/314; 424/315
[58] Field of Search ............... 260/502.5 G, 513 N; 562/571; 424/211, 185, 269, 311, 314, 315

[56] References Cited

U.S. PATENT DOCUMENTS

| | | | |
|---|---|---|---|
| 2,870,201 | 1/1959 | Pollack | 562/571 |
| 3,977,860 | 8/1976 | Franz | 260/502.5 F |
| 4,147,780 | 4/1979 | Dingwall et al. | 260/502.5 G |

FOREIGN PATENT DOCUMENTS 87314  1/1978  Japan ........................ 260/502.5 G

OTHER PUBLICATIONS

Park et al., "Agr. Biol. Chem.", 40(9), pp. 1905, 1906, (1976).
Davies et al., "British Journal of Pharmacology", 70, pp. 52P, 53P, (1980).

*Primary Examiner*—J. E. Evans
*Attorney, Agent, or Firm*—Cushman, Darby & Cushman

[57] ABSTRACT

The (−)-D-isomers of compounds of the general formula

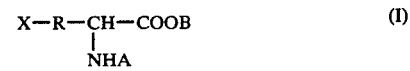

in which
X stands for an acidic radical, especially a radical of phosphonic acid, sulphonic acid, boronic acid or tetrazole,
R stands for an alkylene, alkenylene or alkynylene radical with 3 or more carbon atoms, preferably 3 to 6 carbon atoms, or a $C_3$ to $C_7$ cycloalkyl radical, and
A and B independently of each other stand for a hydrogen atom or a lipophilic radical, especially an ester radical, or salts thereof, or pharmaceutically acceptable bioprecursors thereof, especially (−)-D-aminophosphonopentanoic acid and (−)-D-aminophosphonoheptanoic acid, find use in the treatment of diseases of the central nervous system.

The compound aminophosphonoheptanoic acid is also novel as a racemic mixture and the present invention also relates to that compound in racemic form which may be used in the same way as the said (−)-D-isomers.

14 Claims, No Drawings

AMINO ACID ISOMERS, THEIR PRODUCTION AND THEIR MEDICINAL USE

This is continuation-in-part of Collim et al Ser. No. 356,036 filed Mar. 8, 1982.

The present invention relates to certain new isomers which have use in the treatment of diseases of the central nervous system and to processes for their production.

The compounds of the invention can be administered by intracerebral injection. While this would be a means of administration of last resort in therapy, it has particular significance in research into diseases of the central nervous system. There is much interest currently in developing an understanding of the action of certain compounds produced by the body on the central nervous system (CNS) of vertebrate mammals. Certain receptors in the CNS are excited by amino acids or derivatives thereof. These excitors cause neuronal degeneration and are believed to be responsible for example for Huntington's Chorea disease. Current research is directed at identifying antagonists which block the receptors against excitors. A problem, however, is in determining which receptors are blocked by which antagonists. We have now surprisingly found that (—)-D-amino phosphonoheptanoic acid is a blocker of ibotenic acid-excited receptors but not a blocker of Kainic acid-excited receptors. This compound is therefore of great value in CNS research as a means of blocking ibotenic acid-excited receptors while leaving Kainic acid-excited receptors free to be acted on by candidate antagonists.

According to the present invention we provide, as new compounds, the (—)-D-isomers of compounds of the general formula

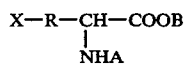  (I)

in which
- X stands for an acidic radical, especially a radical of phosphonic acid, sulphonic acid, boronic acid or tetrazole,
- R stands for an alkylene, alkenylene or alkynylene radical with 3 or more carbon atoms, preferably with 3 to 6 carbon atoms, or a $C_3$ to $C_7$ cycloalkyl radical, and A and B independently of each other stand for a hydrogen atom or a lipophilic radical, especially an ester radical, or salts thereof, or pharmaceutically acceptable bioprecursors thereof.

Among the preferred isomers of the present invention are those in which X stands for a radical of phosphonic acid, A and B stand for hydrogen atoms and R either stands for a propyl or pentyl radical, i.e. (-)-D-aminophosphonopentanoic acid and (-)-D-aminophosphonoheptanoic acid.

The compound aminophosphonoheptanoic acid is also novel as a racemic mixture and the present invention also relates to that compound in racemic form.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

The present invention further relates to processes for the production of compounds of the present invention, in which:

(a) if a compound of formula (I) in which X stands for a phosphonic acid radical is required,
a dibromo compound of the general formula

  (II)

in which,
R has the above-mentioned meaning,
is reacted with a compound of the general formula

  (III)

in which,
R' stands for an alkyl group, preferably an ethyl group,
$M\oplus$ stands for an alkali metal cation, preferably a sodium cation,
and the resulting compound of the general formula

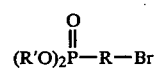  (IV)

is heated, preferably in ethanol, with diethyl acetamidomalonate, and the resulting condensation product of the general formula

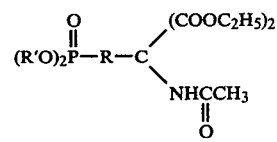  (V)

is subjected to decarboxylation, preferably in boiling hydrochloric acid, or, especially, using iodotrimethyl silane, to give a compound according to the present invention of the general formula

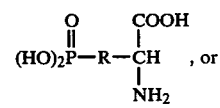  (Ia)

(b) if a compound of formula (I) in which X stands for a sulphonic acid radical is required,
a compound of the general formula

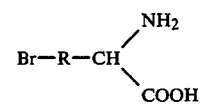  (VI)

in which R has the abovementioned meaning, is reacted with sodium sulphide, to give a compound of the general formula $$\text{HS}-\text{R}-\text{CH}\begin{array}{c}\diagup\text{NH}_2\\\diagdown\text{COOH}\end{array} \quad (\text{VII})$$

which is then heated to give a compound of the general formula $$\begin{array}{c}\text{S}-\text{R}-\text{CH}\begin{array}{c}\diagup\text{NH}_2\\\diagdown\text{COOH}\end{array}\\|\\\text{S}-\text{R}-\text{CH}\begin{array}{c}\diagup\text{NH}_2\\\diagdown\text{COOH}\end{array}\end{array} \quad (\text{VIII})$$

which then is reacted with bromine to give a compound according to the present invention of the general formula $$\text{HO}_3\text{S}-\text{R}-\text{CH}\begin{array}{c}\diagup\text{COOH}\\\diagdown\text{NH}_2\end{array}, \text{ or} \quad (\text{Ib})$$

(c) if a compound of formula (I) in which X stands for a triazolyl radical is required,
a compound of the general formula $$\text{CN}-\text{R}-\text{C}\begin{array}{c}\diagup\text{NHCOCH}_3\\\diagdown(\text{COOC}_2\text{H}_5)_2\end{array} \quad (\text{IX})$$

is reacted with sodium azide to give a compound according to the present invention of the general formula $$\begin{array}{c}\text{N}-\text{N}\\\parallel\quad\diagdown\\\text{N}-\text{N}\diagup\end{array}\text{C}-\text{R}-\text{CH}\begin{array}{c}\diagup\text{NH}_2\\\diagdown\text{COOH}\end{array}, \text{ or} \quad (\text{Ic})$$

(d) if a compound of formula (I) in which X stands for a boronic acid radical is required,
a compound of the general formula, $$\text{MgBr}-\text{R}-\text{Br} \quad (\text{X})$$

in which R has the abovementioned meaning, is reacted with a trialkyl borate, especially triethyl borate, of the general formula $$(\text{R}'\text{O})_3\text{B} \quad (\text{XI})$$

in which R' represents an alkyl group, to give a compound of the general formula $$(\text{R}'\text{O})_2\text{B}-\text{R}-\text{Br} \quad (\text{XII})$$

which is then reacted with a diethylacetamidomalonate and the product of the general formula $$(\text{R}'\text{O})_2\text{B}-\text{R}-\underset{\underset{\text{NHR}}{|}}{\text{C}}-(\text{COOC}_2\text{H}_5)_2 \quad (\text{XIII})$$

is then hydrolysed to give a compound according to the present invention of the general formula $$(\text{HO})_2\text{B}-\text{R}-\underset{\underset{\text{NH}_2}{|}}{\text{CH}}-\text{COOH}; \quad (\text{Id})$$

and the product of reaction variant (a), (b), (c) or (d) of formula (Ia), (Ib), (Ic) or (Id), respectively is, before or after separation of the (−)-D-isomer, converted, if desired into a corresponding compound in which the amino group or carboxylic acid group carries lipophilic group and/or converted into a salt thereof.

Among the new salts of the isomers of the present invention, those salts that are pharmaceutically acceptable are particularly important and are preferred.

The new free isomers of the general formula (I) and their salts can be interconverted in any suitable manner; methods for such interconversion are known in the art.

The separation of the (−)-D-isomer may be carried out by generally known methods, such as reacting the racemic mixture with an optically active base and separating out the salts formed. An appropriate method of separation has been found to be reacting the racemic mixture produced by a process of the invention with L-lysine, thereby forming diastereomers, separating the salt containing the (−)-D-isomer by crystallisation, followed by decomposition of the salt to obtain the (−)-D-isomer.

The starting compounds used in the process variants according to the present invention are known compounds or can be produced by processes similar to those used for the production of such known compounds.

All the process variants are preferably carried out in the presence of an inert organic solvent as the diluent. It is preferred that the reactions are carried out at the boiling point of the solvent used, that is to say, at reflux temperature.

The following reaction schemes illustrate the processes according to the present invention:

$$\text{Br}-\text{R}-\text{Br}\longrightarrow(\text{C}_2\text{H}_5\text{O})_2\overset{\overset{\text{O}}{\parallel}}{\text{P}}-\text{Rbr}\longrightarrow \quad (a)$$

$$(\text{C}_2\text{H}_5\text{O})_2\overset{\overset{\text{O}}{\parallel}}{\text{P}}-\text{R}-\underset{\underset{(\text{COOC}_2\text{H}_5)_2}{|}}{\overset{\overset{\text{NHCOCH}_3}{|}}{\text{C}}}\longrightarrow(\text{HO})_2\overset{\overset{\text{O}}{\parallel}}{\text{P}}-\text{R}-\underset{\underset{\text{NH}_2}{|}}{\text{CHCOOH}}$$

$$\text{Br}-\text{R}-\underset{\underset{\text{NH}_2}{|}}{\text{CH}}-\text{COOH}\overset{\text{H}_2\text{S}}{\longrightarrow}\text{HS}-\text{R}\underset{\underset{\text{NH}_2}{|}}{\text{CHCOOH}}\longrightarrow \quad (b)$$

$$\begin{array}{c}\text{S}-\text{R}-\underset{\underset{\text{NH}_2}{|}}{\text{CHCOOH}}\\|\\\text{S}-\text{R}-\underset{\underset{\text{NH}_2}{|}}{\text{CHCOOH}}\end{array}\overset{\text{Br}_2}{\longrightarrow}\text{HO}_3\text{S}-\text{R}-\underset{\underset{\text{NH}_2}{|}}{\text{CH}}-\text{COOH}$$

-continued

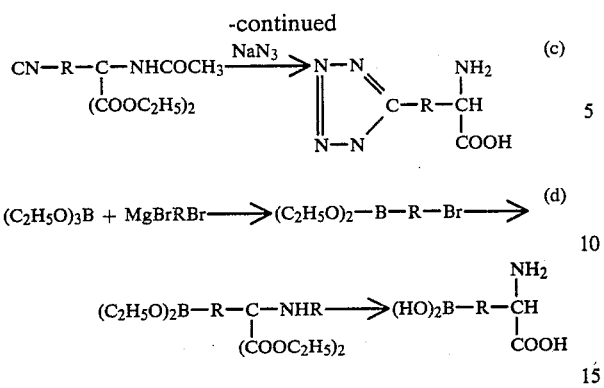 (c)

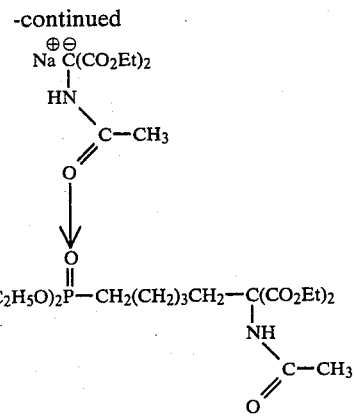

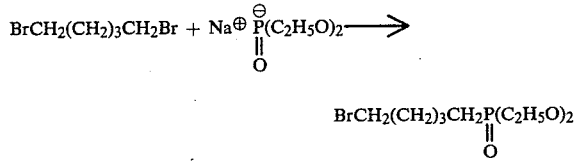 (d)

The isomers of the present invention have use in the treatment of diseases of the central nervous system, particularly Alzheimer's disease and also Huntington's disease and certain forms of epilepsy. Those isomers which comprise lipophilic radicals may be applied by conventional pharmaceutical administration routes such as parenteral administration, e.g. intravenous administration.

The following Example illustrates a process for the production of an isomer of the present invention.

EXAMPLE 1

(a) Synthesis of (31)2-amino-7-phosphonoheptanoic acid 1,5-dibromopentane → diethyl-5-bromopentane phosphonate $$BrCH_2(CH_2)_3CH_2Br + Na^\oplus \overset{\ominus}{\underset{\overset{\|}{O}}{P}}(C_2H_5O)_2 \longrightarrow$$

$$BrCH_2(CH_2)_3CH_2\underset{\overset{\|}{O}}{P}(C_2H_5O)_2$$

Diethyl phosphite was dissolved in anhydrous diethyl ether, and an equimolar quantity of sodium added in small pieces over a period of ½ hr; hydrogen being given off during this reaction. Four mole equivalents of 1,5-dibromopentane were dissolved in anhydrous diethyl ether, and the sodium salt of diethyl phosphite added, as a suspension, with stirring. The mixture was stirred for 36 hours, then refluxed for 2 hours; during this process, the fine precipitate of NaBr flocculated, and was filtered off. The ether was evaporated off to leave a colourless liquid. Excess dibromopentane was distilled off at 1 mm Hg, to leave a colourless oil which was taken up in 50/50 pet.ether/ether and columned on Kieselgel 60 in 50/50 pet. ether/ether. The first fraction contained unreacted diethyl phosphite; the product came off in pure diethyl ether.

(b) Diethyl-5-bromopentane phosphonate→acetamido adduct

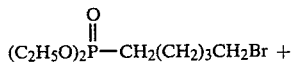 +

-continued

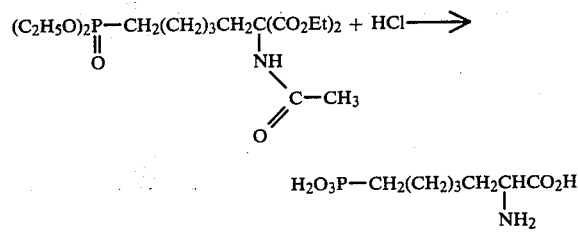

The sodium salt of diethyl acetamidomalonate, was prepared by dissolving sodium in a slight excess of ethyl alcohol, and adding an equimolar quantity of diethyl acetamido malonate. The mixture was refluxed until a brown colouration indicated the formation of the sodium salt. The ethyl alcohol was evaporated off at 80° C., in vacuo, to leave a tan syrup; the remaining alcohol was removed by successive distillations with dry toluene, to leave a tan solid. The sodium salt was suspended in dry toluene, and diethyl carbonate added; the diethyl-5-bromopentane phosphonate was added, and the mixture refluxed for 3 days. The resulting NaBr was filtered off, and the solvents evaporated to leave a sticky, dark brown syrup. This was taken up in diethyl ether and columned on Kieselgel 60. Unreacted diethyl acetamido malonate, and diethyl-5-bromopentane phosphonate, came off with diethyl ether, and were separated by crystallisation of diethyl acetamido malonate from ether solution. The product was eluted off the column with chloroform, as a light yellow viscous syrup.

(c) Acetamido adduct→(±)2-amino-7-phosphonoheptanoic acid $$(C_2H_5O)_2\underset{\overset{\|}{O}}{P}-CH_2(CH_2)_3CH_2\underset{\underset{\underset{\overset{\diagdown}{C}-CH_3}{\overset{\|}{O}}}{NH}}{C}(CO_2Et)_2 + HCl \longrightarrow$$

$$H_2O_3P-CH_2(CH_2)_3CH_2\underset{NH_2}{CH}CO_2H$$

The acetamido adduct was refluxed together with 6M HCl overnight; the solution was evaporated to dryness, and the solid taken up to 5% aqueous ethanol. The free acid was precipitated by careful addition of propylene oxide and filtered off. The acid was dissolved in water and passed down on "Dowex" 50×8 (H÷) column. The acid was washed with 5 bed volumes of water followed by elution with 2M aqueous pyridine. The amino acid containing fractions were evaporated to dryness, and the product recrystallised from water/ethenol.

(d) Resolution of 2-amino-7-phosphonoheptanoic acid

Equimolar quantities of the phosphonic acid, and L-lysine, were dissolved in water and warmed for ½hr at 60° C. Two volumes of hot methanol were then added and the mixture brought to room temperature. Diethyl ether was added carefully, until a slight cloudiness appeared in the solution, which was left to stand. The phosphonic acid/lysine salt was filtered off and dissolved in water. A "Dowex" 50×8 column was prepared by passed 2M pyridine down it, and washing with water, the lysine salt solution was passed down the column and washed through with water, the phosphonic acid passing straight through. The amine acid containing fractions were collected and evaporated to dryness; a solution of known concentration was then made up, and the rotation of plane polarised light recorded on a "TBL" Automatic Polarimeter 143D using a mercury lamp. The first isomer to be precipitated was found to be (−), and circular dichroism studies indicated it to have the D configuration.

EXAMPLE 2

Synthesis of (−)2-amino-7-sulphonoheptanoic acid (a) Preparation of diethyl acetamido adduct of 1,5-dibromo pentane 0.04 mol of the sodium diethyl acetamido malonate were reacted with 0.2 mol of dibromopentane, Br-$(CH_2)_5$-Br (I). The product was isolated after filtering off the NaBr by evaporation of the solvent, and vacuum distillation of the resulting liquid to drive off the excess dibromopentane. The remaining oil was columned on silica, residual dibromopentane being brought off in 1:1 diethyl ether:petroleum ether, the product following this using the same eluant; unreacted diethyl acetamido malonate was removed from the column by changing the eluent to pure diethyl ether. The product, a white crystalline solid from ether/petroleum ether; m.pt. 50° C.; yield 0.0186 mol (47%).

A sample was submitted for $^{13}C$ NMR analysis:

$$^{13}C\ NMR:\ Br\underset{1}{-}CH_2\underset{2}{-}CH_2\underset{3}{-}CH_2\underset{4}{-}CH_2\underset{5}{-}CH_2\underset{6}{-}C(CO_2Et)_2 \atop NH-CO-CH_3 \quad (II)$$

| carbons 1 to 5 | 23.4; 28.4; 32.7; 33.0; 34.15 ppm |
| --- | --- |
| carbon 6 | 57.12 ppm |
| acetamido CH$_3$ | 67.1 ppm |
| ester CH$_3$ | 14.6 ppm |
| ester O—CH$_2$ | 62.9 ppm |
| ester carboxyl C=O | 168.8 ppm |
| acetamido carbonyl C=O | 170.9 ppm rel TMS |

(b) Preparation of 2-amino-7,7'-dithiobisheptane carboxylic acid:

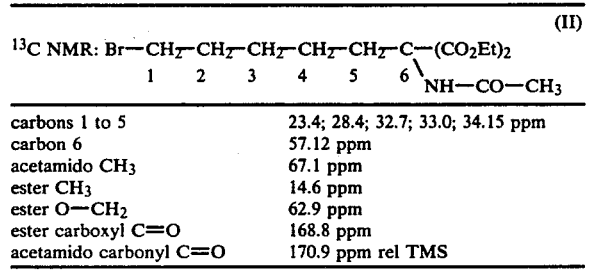

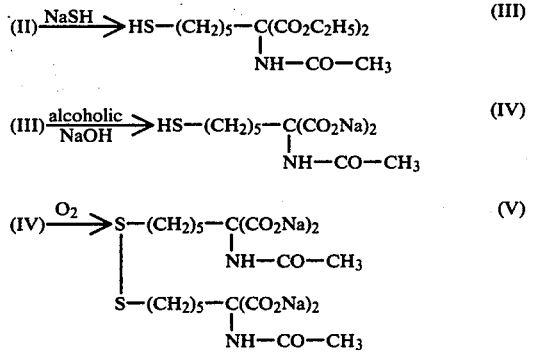

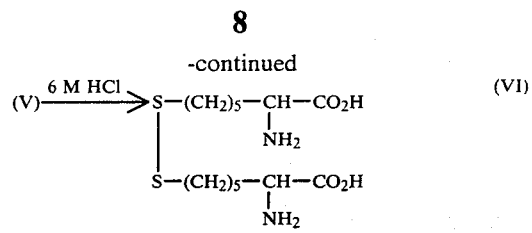

The diethyl acetamidobromo alkane dicarboxylate (II) from preparation (a) was converted into the diethyl acetamido thioalkane dicarboxylate (III) which in turn was converted into the acetamido thioalkane dicarboxylic acid sodium salt (IV). The latter was converted into the acetamido dithiobis-alkane dicarboxylic acid (V) which in turn was converted into the 2-amino-dithiobis-alkane carboxylic acid (VI). This series of reactions was carried out precisely as described by du Vigneaud et al with no deviations. (When preparing the compound (III), the reagent NaSH was prepared by bubbling H$_2$S through a solution of sodium sulphide (dissolved in its own water of crystallisation). It was found necessary to exclude additional moisture in order to avoid hydrolysis of the reactive sodium hydrosulphide). See Journal of Biological Chemistry, Vol 106, pp 401–407 (1934).

The product, which was isolated by neutralisation of the final acid solution with 5 M NaOH, precipitated as a white solid which was crystallised from water.

Yield 0.0047 mol (25%).

Analysis: Calculated for $C_{14}H_{28}N_2O_4S_2$: C 44.77; H 7.95; N 7.95; S 19.25; found: C 46.64; H 7.74; N 7.88.

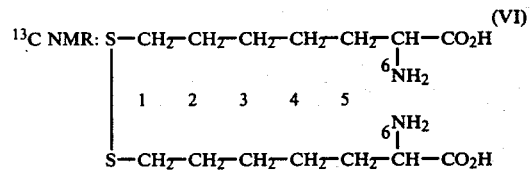

carbons 1 to 5 24.5; 27.8; 28.7; 30.4; 38.83 ppm
carbon 6 53.7 ppm
carboxyl C=O 173.0 ppm rel TMS.

(c) Bromine-water oxidation of the dithiobis amino acid (VI).

The dithiobis amino acid, was suspended as a fine powder in distilled water and placed on a magnetic stirrer. Bromine was added drop by drop; with each addition, time was allowed for the bromine to disperse and for the yellow colouration to disappear. Towards the end of the reaction all the dithiobis amino acid went into solution and the yellow colouration persisted for longer periods. When the point was reached when the colouration persisted for longer than 1 hour the reaction was complete. The solution was evaporated to near dryness at 60° C. on a rotary evaporator and the brown fuming residue taken up in ethanol. The bromide salt was destroyed by careful addition of propylene oxide, the product precipitating out of solution as a white sticky solid.

The solid was dissolved in a small amount of water and placed on an Amberlite IRA 45 column. The column was washed with 3 bed volumes of water and the amino acid then eluted with 5 M acetic acid. The amino acid-containing fractions were combined and evaporated to dryness; the residual acetic acid was driven off by repeated solution and evaporation. The sulphono amino acid was recrystallised from water and ethanol to give a white crystalline solid. M.pt. 239°–241° C. (dec); yield 0.0045 mol (93%).

Analysis: calculated for $C_7H_{15}NO_5S$: C 37.3; H 6.67; N 6.62; S 14.22; found: C 36.9; H 6.64; N 6.53; S 14.1.

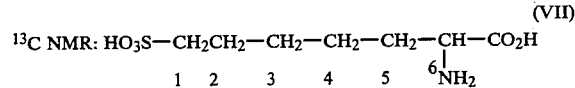
(VII)

carbons 2 to 5, 24.6; 28.06; 30.61; 31.2 ppm
carbons 1 to 6, 51.68; 54.28 ppm
carboxyl C=O, 173.74 ppm rel TMS (d) Resolution of (-)2-amino-7-sulphonoheptanoic acid (VII)

0.02 mol of the sulphono heptanoate were dissolved in water with 0.02 mol of L-lysine. The solution was warmed at 60° C. for 1 hour; two volumes of hot methanol were added and the volume of water was adjusted as the methanol was added, to prevent immediate precipitation. On standing, the solution began to precipitate a small quantity of flocculant material; this was filtered off and the remaining solution treated with diethyl ether until a slight turbidity was seen in the solution. The first salt crystallised out after standing for 2 hours and was filtered off. The salt was taken up in water and passed through an Amberlite IRA 45 [$OH^-$] ion-exchange resin column. The column was washed with 3 bed volumes of water until no further ninhydrin-staining material was present in the washings. This material was analysed by TLC and found to be identical to a sample of L-lysine run at the same time. The column was then washed through with 5 M aqueous acetic acid and all the ninhydrin-staining fractions collected. The combined solution was evaporated to dryness and the residual acetic acid was driven off by repeated solution and evaporation. A TLC of the product proved to be identical to a sample of ± aminosulphono heptanoate.

The compound was made up in a solution of concentration 10 g/100 ml; the rotation was measured in a Thorn automatic polarimeter at 546 nm.

Rotation of 2-amino-7-sulphonoheptanoate, first out of solution

Blank=0.00°
Sample=−0.112°
$\alpha_{546}^{25} = -5.6°$.

The mother liquor was passed through a column of Amberlite [$OH^-$] and washed with water. The product was eluted with 5 M aqueous acetic acid and the product isolated as above. A TLC of the product proved to be identical to a sample of ± aminosulphonoheptanoate. The sample was made up to 10 g/100 mls of water and the rotation determined as above.

Rotation of 2-amino-7-sulphonoheptanoate, second out of solution

Blank=0.00°
Sample=+0.101°
$\alpha_{546}^{25} = +5.05°$

Examples 1 and 2 illustrate the production of a compound wherein R is saturated. The following example relates to the production of a compound wherein R is unsaturated.

EXAMPLE 3

(a) Preparation of bromophosphonate

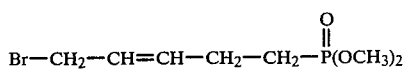

Butyl lithium (50 mmols) was slowly added to a solution of dimethyl methylphosphonate (6.2 gms, 50 mmols) in dry tetrahydrofuran (120 mls), under nitrogen, at −78° C. The temperature was kept below −70° C. during the addition. The mixture was stirred for a further 10 mins. at −78° C., after addition and then dibromobutene (12.84 gms, 60 mmols) in dry tetrahydrofuran (100 mls) was gradually added. The temperature was again kept below −70° C. After the addition the mixture was allowed to warm to room temperature and left to stir overnight.

The solvent was removed, in vacuo, and the residue dissolved in water (120 mls) and extracted with ether (4×100 mls). Drying over MgSO₄, filtration and evaporation of the solvent, in vacuo, afforded a yellow oil which was chromatographed on silica gel (450 gms) using, initially, ethyl acetate as eluant and then ethyl acetate/ethanol (5:1 and 4:1). The initial fraction was unreacted bromobutene, the second pure bromophosphonate (7.35 gms, 42%).

(b) Preparation of diethyl acetamidomalonate adduct

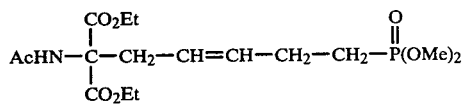

To a solution of sodium diethyl acetamidomalonate (230 mg sodium, 2.17 gms malonate, 10 mmols) in methanol (30 mls), under nitrogen, the bromophosphonate (2.57 gms, 10 mmols), prepared previously, in methanol (10 mls) was slowly added at room temperature. The mixture was then heated under reflux for 24 hrs.

After evaporation of the solvent, in vacuo, the residue was dissolved in water (30 mls) and extracted with ethyl acetate (4×50 mls). Drying over MgSO₄, filtration, and evaporation of the solvent, in vacuo, gave a dark yellow oil. Chromatography on silica gel (50 gms) using initially ethyl acetate (to remove any unreacted malonate) and then ethyl acetate/ethanol (5:1 3:1) gave pure acetamido adduct (3.15 gms, 81%).

(c) Preparation of amino acid

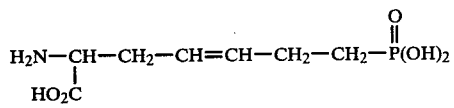

The acetamido adduct (1.98 gms, 5 mmols) was dissolved in 6M HCl (25 mls) and the solution heated under reflux for 18 hrs. The solvent was then evaporated in vacuo, and the amino acid isolated by ion-exchange methods (Dowex 50W—X8 resin). Recrystallization from water/methanol afforded the pure acid (770 mgs, 70%).

As indicated previously, the present invention further relates to a method of blocking ibotenic acid-excited receptors but not blocking kainic acid-excited receptors comprising administering to a vertebrate mammal an amount of active compound of the invention effective to block ibotenic acid-excited receptors but not block kainic acid-excited receptors.

The following biotest Example merely serves to illustrate this further aspect of the present invention.

EXAMPLE A

Dicarboxylic amino acids and their thio-analogues were tested as potential anticonvulsants in animal models of epilepsy by being administered intracerebroventricularly (i.c.v.) or intraperitoneally (i.p.) in mice (either DBA/2 mice showing sound-induced seizures, or Swiss S mice given a just-convulsant dose of pentylenetetrazol, s.c.) or intravenously in baboons, Papio papio, with photosensitive epilepsy. A close correlation was found between the ability of antagonists to block excitation due to NMDA (N-methyl-D-aspartic acid) and suppression of sound-induced seizures following i.c.v. injection in DBA/2 mice. For a congeneric series of phosphonic acid analogues of dicarboxylic amino acids, the order of potency was 2-amino-7-phosphonoheptanoate>2-amino-5-phosphonopentanoic acid>2-amino-6-phosphonohexanoic acid>2-amino-4-phosphonobutyric acid. Glutamic acid diethyl ester, a quisqualate receptor antagonist was inactive. γ-D-glutamylglycine, an antagonist of both kainate and NMDA-induced excitation was equipotent with 2-amino-5-phosphonoheptanoic acid. Following systemic administration in mice 2-amino-7-phosphonoheptanoic acid was active against sound-induced seizures (0.1–0.33 mmoles/kg, i.p.) and against pentylenetetrazol seizures (1.2 mmoles/kg). It is also active against photosensitive epileptic responses in baboons (1.0 mmoles/kg, i.v.)

The administration was carried out in detail as follows:

(i) Anticonvulsant activity of excitatory amino acid antagonists in DBA/2 mice DBA/2 mice were chosen as being an inbred strain in which, within a critical age range, a fixed sequence of seizure response can be induced by a loud sound. Groups of DBA/2 mice (N=6 to 10), 21 to 28 days old, were injected intracerebroventricularly under light ether anesthesia with 10 μl of drug solution or phosphate buffer alone (pH 7.3). Auditory stimulation (electric bell generating 109 dB at mouse level) was applied 45 minutes later for 60 seconds or until tonic extension was observed and the incidence and timing of the phases of the seizure response were recorded. These included an initial wild running phase (WR) followed by myoclonus, tonic flexion, and extension and, frequently, respiratory arrest. Seizure response was scored as described in Eur. J. Pharmacol 59, 75 (1979), and comparisons between groups of control and drug-treated animals were made by using Fisher's exact probability test. Successive doses, with a geometric factor of 3, were tested until an adequate log dose-response curve (three to six points) could be constructed for each antagonist for each phase of the seizure response, and $ED_{50}$ values were graphically determined. A rank order of anticonvulsant potency was allocated to each antagonist for comparison with iontophoretic data; O denoting no activity and X to XXXX denoting increasingly marked activity.

| Antagonist | Minimum dose to suppress WR* (μ mole) | $ED_{50}$ (μ mole) | | | Relative anti-convulsant potency | Relative NMDA antagonist potency* |
|---|---|---|---|---|---|---|
| | | WR | Clonus | Tonus | | |
| Comparative compounds | | | | | | |
| D-α-Aminoadipic acid | (0.25)++ | | | | O | |
| Glutamic acid diethylester | (3.3)++ | | | | O | |
| γ-D-Glutamylglycine | 0.1 | 0.058 | 0.046 | 0.054 | X | |
| (±)-2-Amino-4-phosphonobutyric acid | (0.5)++ | | | | O | X |
| Compounds of the invention | | | | | | |
| (±)-2-Amino-5-phosphonopentanoic acid | 0.1 | 0.046 | 0.022 | 0.025 | X | XX |
| (±)-2-Amino-6-phosphonohexanoic acid | 0.25 | 0.17 | 0.14 | 0.15 | X | X |
| (±)-2-Amino-7-phosphonoheptanoic acid | 0.01 | 0.004 | 0.018 | 0.0008 | XXX | XXX |
| (+)-2-Amino-7-phosphonoheptanoic acid | 0.033 | 0.0135 | 0.0018 | 0.0018 | XX | XX |
| (−)-2-Amino-7-phosphonoheptanoic acid | 0.0033 | 0.0022 | 0.0008 | 0.0008 | XXXX | XXXX |

*$P < .01$.
++Inactive

(ii) Effect of (±)-2-amino-7-phosphonoheptanoic acid on audiogenically induced and pentylenetetrazol-induced seizures in mice Studies of audiogenic seizures were performed as described in Example(i). For intraperitoneal administration the antagonist was injected with 0.1 ml of saline 45 minutes before testing. Antagonism of pentylenetetrazol (PTZ: threshold) seizures was studied in random-bred Swiss mice (Tuck T/O strain: 28 days old; 20 to 23 g). Mice in groups (N=10) received pentylenetetrazol (85 mg/kg: 0.85 percent solution in 0.9 percent sodium chloride) subcutaneously in a loose fold of skin on the back of the neck 45 minutes after intracerenroventricular or intraperitoneal administration of drug or vehicle. During the 30-minute observation period sustained rhythmic clonic jerking with tonic spasms occured in 90 to 100 percent of control mice. The incidence and timing of clonic episodes was recorded with absence of sustained clonic jerking (no episode of 5 seconds duration or longer) being defined as protection. The $ED_{50}$ values and 95 percent fiducial limits were estimated by using the method of moving averages (by the method described in Biometrics 8, 249 (1952) with data from four successive dose levels.

| Antagonist | Route of administration | Minimum dose to suppress WR* | ED$_{50}$ WR* Clonus Tonus | ED$_{50}$ V PTZ (95% fiducial limits) |
|---|---|---|---|---|
| (±)-2-Amino-7-phos-phonoheptanoic acid | Intracerebro-ventricular | 0.01 μ mole | 0.004 0.0018 0.0008 | 0.64 (0.19–2.13) μ mole |
|  | Intraperitoneal | 0.33 mmole/kg | 0.18 0.04 0.04 | 1.18 (0.97–1.43) mmole/kg |

*P < .01.

It is surprising that the (−)-D-isomers of the present invention should exhibit activity as anticonvulsants. The required dosage levels compare favourably to those of known drugs used for epilepsy. The spectrum of activity of the present compounds and the routes by which they can be administered are especially remarkable. In particular it is surprising that the active compounds can pass the blood-brain barrier to permit intraperitoneal and intravenous administration in addition to intracerebroventricular administration. (Thus, even the possibility of oral administration seems worth investigating.) Thus the compounds of this invention are an unexpected advance in the art.

What is claimed is:

1. A method of combatting a disease of the central nervous system in a human and non-human animal which comprises administering to the animal the (−)-D-isomer of aminophosphonoheptanoic acid or an ester or a salt thereof, or a pharmaceutically acceptable bioprecursor thereof effective to combat the disease.

2. A method according to claim 1 in which the active compound is administered by intracerebral injection.

3. A method according to claim 1, wherein there is administered, (−)-D-aminophosphonoheptanoic acid, or a racemic mixture of aminophosphonoheptanoic acid.

4. A method according to claim 1 wherein the compound is free of the (+) isomer.

5. A method according to claim 4 wherein there is administered (−)-D-aminophosphonoheptanoic acid.

6. A method according to claim 1 wherein there is administered (−)-D-aminophosphonoheptanoic acid, a salt thereof or an ester thereof.

7. A method according to claim 6 wherein the compound is free of the (+) isomer.

8. A method according to claim 1 wherein there is administered (D)-aminophosphonoheptanoic acid.

9. A method of blocking ibotenic acid-excited receptors comprising administering to a vertebrate mammal an amount of the (−)-D isomer of aminophosphonoheptanoic acid or an ester of a salt thereof, or a pharmaceutically acceptable bioprecursor thereof effective to block ibotenic acid-excited receptors but not block kainic acid-excited receptors.

10. A method according to claim 9 wherein the compound is free of the (+) isomer.

11. A method according to claim 9 wherein there is administered (−)-D-aminophosphonoheptanoic acid, a salt thereof or an ester thereof.

12. A method according to claim 11 wherein the compound is free of the (+) isomer.

13. A method according to claim 11 wherein there is administered (−D)-aminophosphonoheptanoic acid.

14. A method according to claim 13 wherein the compound is free of the (+) isomer.

* * * * *